(12) United States Patent
Zakarian et al.

(10) Patent No.: US 6,605,301 B2
(45) Date of Patent: Aug. 12, 2003

(54) DISPERSIBLE MACROLIDE COMPOUNDS AND METHOD FOR PRODUCTION THEREOF

(75) Inventors: Noël Zakarian, Marseille (FR); RenéGimet, Valbonne (FR); Claude Laruelle, Villeneuve-Loubet (FR); Dominique Toselli, Nice (FR)

(73) Assignee: CCL Pharma (FR)

( * ) Notice: Subject to any disclaimer, the term of this patent is extended or adjusted under 35 U.S.C. 154(b) by 0 days.

(21) Appl. No.: 09/966,669

(22) Filed: Sep. 28, 2001

(65) Prior Publication Data

US 2002/0061333 A1 May 23, 2002

(51) Int. Cl.$^7$ .............................. A61K 9/20; A61K 9/16
(52) U.S. Cl. ...................... 424/464; 424/464; 424/465; 424/490
(58) Field of Search ................................ 424/490, 464, 424/465

(56) References Cited

U.S. PATENT DOCUMENTS 5,106,967 A * 4/1992 Mazur et al. ................ 536/119
5,192,752 A * 3/1993 Chapura et al. ............. 514/152

FOREIGN PATENT DOCUMENTS

EP        0 679 400      * 11/1995   .......... A61K/31/71

OTHER PUBLICATIONS

International PCT Patent Application No. PCT/FR00/00800, filed Mar. 20, 2000, International Publication No. WO 00/57886, published Oct. 5, 2000.
PCT International Search Report.
English translation of International PCT Patent Application No. PCT/FR00/00800, filed Mar. 20, 2000, International Publication No. WO 00/57886, published Oct. 5, 2000.
Notification of transmission of priority document (Notification Relative A La Presentation Ou A La Transmission Du Document De Priorite).
PCT Chapter II Demand (Avis Informant Le Deposant De La Communication De La Demande Internationale Aux Offices Designes).
PCT International Preliminary Examination Report (Traite De Cooperation En Matiere De Brevets PCT Rapport D'Examen Preliminaire International).
International Application No. PCT/FR93/00945, filed Sep, 28, 1993, International Publication No. WO 94/07504, ublished Apr. 14, 1994, of Rhome–Poulenc Rorer S.A. pertains to New Pharmaceutical Formulations of Spiramycine.
International Application No. PCT/EP91/00689, filed Apr. 9, 1991, International Publication No. WO 91/16043, published Oct. 31, 1991, of Eurand International SPA pertains to Pharmaceutical Formulations.
European Application No. 95302628.3, filed Apr. 20, 1995, Publication No. 0 679 400 A1, published Nov. 2, 1995 of Pfizer Limited, pertains to the Oral Dosage Forms of Azithromycin Avoiding Drugfood Interaction.

* cited by examiner

Primary Examiner—Thurman K. Page
Assistant Examiner—Micah Paul Young
(74) Attorney, Agent, or Firm—Welsh & Katz, Ltd.; Thomas W. Tolpin

(57) ABSTRACT

The invention relates to dispersible tablets containing macrolides as active ingredients either on their own or associated with other active ingredients, in addition to a method for the production thereof. The dispersible tablets are characterized in that the macrolide is chosen from a group that is made up of pristinamycin, azithromycin, roxithromycin, clarithromycin and spiramycin, and is present in a basic form in proportions ranging from 20–60% of the total weight of said tablets. The dispersible tablets are also characterized in that they contain at least one disintegrator in proportions ranging from 1–25% of the total weight of said tablets in addition to at least one sweetening agent.

16 Claims, No Drawings

DISPERSIBLE MACROLIDE COMPOUNDS AND METHOD FOR PRODUCTION THEREOF

BACKGROUND OF THE INVENTION

The present invention relates to dispersible tablets containing macrolides as active ingredients, alone or combined with other active ingredients, and their method of preparation.

The present invention relates more particularly to dispersible tablets containing azithromycin, roxithromycin or clarithromycin as active ingredients, alone or combination with other active ingredients.

In therapy, the simplicity of using tablets has always been considered as a major advantage in particular in the context of ambulatory treatments, as demonstrated by the very large number of proprietary medicinal products which are provided in this form.

However, some patients and, in particular, children and the elderly experience deglutition difficulties such that it is difficult and consequently unpleasant for them to ingest tablets, even with a dose combined with liquid.

That is the reason why it is desirable to have available tablets capable of disintegrating in a small volume of liquid, so as to be able to be ingested in the form of solutions or suspensions which can be taken orally.

However, numerous active ingredients are known to exhibit a bitterness which is very difficult to mask, when they are provided in the form of solutions or suspensions to be taken orally.

This is the case in particular with macrolides, whether they are used alone or in combination with other active ingredients. Macrolides have in common the feature of comprising a central lactonic nucleus consisting of 14 to 16 members with few or no double bonds and no nitrogen. One or more amino and/or neutral sugars (desosamine, cladinose, mycarose, mycaminose) are attached by $\alpha$- or $\beta$-glycosidic bonds to this nucleus, also called aglycone. There may be mentioned as macrolides natural derivatives, erythromycin A to F, oleandomycin, spiramycin, midecamycin and troleandomycin and as semisynthetic macrolides, roxithromycin, dirithromycin, clarithromycin, flurithromycin and rokitamycin. The 15-membered azolides, which possess an endocyclic nitrogen atom, such as azithromycin also form part of the macrolides [A. Bryskier, 1995, in *Le bon usage des macrolides*, page 8, Classification des macrolides (Classification of the macrolides), Ed. Phase 5].

However, this bitterness is marked to a greater or lesser degree depending on the physicochemical characteristics of the macrolide. For example, troleandomycin is practically free of bitterness [*Traité de chimie therapeutique*, 1992, vol. 2, Médicaments Antibiotiques (Antibiotic drugs) TEC & DOC Lavoisier, Editions Médicales Internationales], whereas pristinamycin, azithromycin, roxithromycin, clarithromycin and spiramycin have a very pronounced bitterness.

Accordingly, numerous techniques have been proposed for masking the bitterness of these active ingredients and in particular that of roxithromycin, clarithromycin and spiramycin.

In general, these techniques consist either in carrying out a more or less complex coating of the active ingredient (French patent application No. 2 669 533; international application No. WO 97/16174), or simply in trying to mask the taste by the use of a suitable sweetener, most often combined with a large quantity of sucrose (French patent application No. 2 696 346; proprietary medicinal product Rulid® 50 mg, powder for suspension which can be taken orally).

Thus, French patent application No. 2 669 533 describes a method for the manufacture of dispersible granules containing spiramycin and intended to mask the taste of this active ingredient. In this method, the spiramycin encapsulated in albumin by a technique which requires the use of organic solvents such as isooctane and their removal at the end of the method, and then the capsules thus obtained are diluted with a mixture of sugars (lactose+fructose). The technique for the encapsulation of spiramycin, although effective, is very expensive because it only allows the manufacture of small quantities of pharmaceutical composition, and requires long and expensive steps for the recycling of solvents.

That is why international application No. WO 97/16174 provides, for its part, a method which makes it possible to prepare dispersible granules of a macrolide and, for example, of clarithromycin, without the use of organic solvents. In this method, the macrolide is subjected to granulation after mixing with a polymer of branched acrylic acid with high crosslinking power. This granulation is carried out in the presence of water and is optionally followed by a second granulation which, for its part, is carried out in the presence of an aqueous solution of a binding agent such as polyvinylpyrrolidone.

French patent application No. 2 696 346 also proposes preparing spiramycin formulations with enhanced taste and provided in the form of granules to be dissolved or to be dispersed in water. These formulations contain a particular sweetener, namely acesulfame potassium, and sucrose in a high proportion—since the spiramycin/sucrose weight ratio is between 1/1 and 1/9—in order to mask the bitterness of the spiramycin.

However, the latter formulations, just like the formulations obtained by coating as proposed in FR-A-2 669 533 and WO-A-97/16174, exhibit certain disadvantages and, in particular, that of not sufficiently masking the bitterness of the macrolides which they contain. Furthermore, the quantities of sugar(s) present in the formulations described in FR-A-2 669 533 and FR-A-2 696 346 make the administration of these formulations contraindicated in diabetic patients.

Recently, a dispersible tablet, with no coating and free of sugar, has indeed been proposed for josamycin (dispersible JOSACINE®), but the latter is known to have a taste which is a lot less bitter than the other macrolides and to exhibit no technical difficulty for the formulation. In this tablet, the josamycin is present in propionate form, in a quantity corresponding to 50% of the total weight of said tablet.

However, to date, no dispersible tablet free of sugar and having a suitable taste has ever been provided for the most bitter macrolides such as spiramycin, roxithromycin, clarithromycin, pristinamycin and azithromycin.

Consequently, the inventors set themselves the aim of remedying this fault and of developing dispersible tablets which contain active ingredients and, in particular, very bitter macrolides, and which, although free of sugars, lead, when they disintegrate in water, to oral suspensions having a completely acceptable taste so that these suspensions are not unpleasant to swallow.

BRIEF SUMMARY OF THE INVENTION

The subject of the present invention is therefore dispersible tablets which contain a macrolide as active ingredient, alone or in combination with another active ingredient, which tablets are characterized in that the macrolide is chosen from the group consisting of pristinamycin, azithromycin, roxithromycin, clarithromycin and spiramycin, and is present in base form, in proportions of between 20% and 60% of their total weight, and in that they comprise at least one disintegrant, in proportions of between 1% and 25% of their total weight, and at least one sweetener.

For the purposes of the present, the expression "dispersible tablets" is understood to mean tablets capable of completely disintegrating in less than 3 minutes when they are placed in a liquid such as water, and of thus leading to an oral suspension that can easily be made homogeneous by stirring it, for example, using a teaspoon. Such tablets may however be also swallowed directly with a quantity of liquid capable of facilitating their deglutition.

In spite of the absence of sugars and, in particular, of sucrose, the tablets in accordance with the invention surprisingly have a markedly more pleasant taste than that presented by the dispersible powders and granules provided up until now for the bitter macrolides, even when they contain high quantities of macrolide.

A more detailed explanation of the invention is provided in the following description and appended claims.

DETAILED DESCRIPTION OF THE INVENTION

A dispersible tablet and its composition and uses according to the preferred embodiments of the present invention will now be explained.

According to a first advantageous feature of the invention, the macrolide used is chosen from the group consisting of azithromycin, roxithromycin and clarithromycin.

The disintegrant is the agent which allows the tablets to disintegrate completely in the presence of a liquid, this being in a relatively short time since less than 3 minutes, and the active ingredient(s) to be released into this liquid; its choice is therefore particularly important.

Accordingly, according to another advantageous feature of the invention, the disintegrant is chosen from the group consisting of polyvinylpyrrolidone, croscarmellose sodium and mixtures thereof.

According to a particularly preferred feature of the invention, polyvinylpyrrolidone is used in proportions of between 1% and 16% of the total weight of the tablets, or croscarmellose sodium in proportions of between 1% and 15% of the total weight of the tablets or alternatively the mixture of both in a ratio of between 1:1 and 4:1.

According to yet another advantageous feature of the invention, the sweetener is chosen from the group consisting of aspartame, saccharin sodium, acesulfame potassium, ammonium glycerinate and mixtures thereof.

According to a preferred embodiment of the invention, a mixture of two sweeteners is used in a ratio of between 1:1 and 2:1, said mixture representing, by weight, between 1 and 20% of the total weight of the tablets.

According to another preferred embodiment of the invention, the macrolide is combined with a nitroimidazole derivative. By way of examples of such derivatives there may be mentioned metronidazole, tinidazole or ornidazole.

In this case, the macrolide is preferably spiramycin while the nitroimidazole derivative is preferably metronidazole.

In addition to a macrolide, a disintegrant and a sweetener, the tablets according to the invention contain other excipients, in proportions which are chosen according to the physicochemical properties of the macrolide which they contain.

These excipients are chosen from the group consisting of diluents, surfactants, lubricants and glidants.

The tablets contain, in addition, at least one flavoring which contributes to give them a taste which is acceptable to the patient.

The diluents facilitate the compressing operations necessary for producing tablets and give sufficient hardness to the latter.

According to the invention, the diluent(s) may be chosen in particular from the group consisting of microcrystalline cellulose, lactose, hydroxypropyl methyl cellulose (HPC) and pregelatinized starch. Preferably, microcrystalline cellulose is used in proportions of between 5% and 50% of the total weight of the tablets.

The tablets according to the invention also contain one or more surfactants, for example polysorbates or sodium lauryl sulfate, in proportions of between 0.1% and 3% of their total weight.

They also contain one or more lubricants such as magnesium stearate and calcium stearate. These lubricants, whose role is to reduce friction during the compressing operations, are advantageously present in proportions of between 0.5 and 5% of the total weight of the tablet.

Among the glidants which can be included in the tablets according to the invention, there may be mentioned in particular colloidal silica, talc, stearic acid and magnesium stearate; these glidants, which prevent the components of the tablets from forming aggregates during the preparation of these tablets and which also reduce friction during the compressing operations, are present of proportions of between 0.1% and 3% of the total weight of the tablets.

The flavoring(s) are chosen according to the age of the patients (adults or children) for whom the tablets are intended and are present in proportions of between 0.5% and 15% of the total weight of these tablets.

Among the flavorings which can be used, there may be mentioned mint, chocolate, caramel, vanilla, strawberry and licorice flavors and mixtures thereof.

The mint and vanilla/caramel flavors are particularly preferred. The mint flavor is generally present in proportions of between 1% and 7% of the total weight of the tablets, while the vanilla/caramel flavor is, for its part, present in proportions of between 1% and 10% of the total weight of said tablets.

The dispersible tablets according to the invention offer the following advantages:

ease of use in ambulatory treatment, accuracy of the unit dosage, ease of dispersion in a liquid, pleasant taste, ease of deglutition in case of direct ingestion, that is to say without prior dispersion in a liquid, absence of sugars and, in particular, of sucrose, making them particularly suitable for the treatment of diabetic patients.

The subject of the invention is also a method for preparing dispersible tablets as defined above, which method is characterized in that it comprises:

the mixing of the active ingredient(s) with 30% to 60% of the quantity of disintegrant(s) intended to be present in the tablets, the wet granulation of the resulting mixture in the presence of a wetting liquid containing water and at least one surfactant, the drying of the granules thus obtained, the dry addition of the remaining 40 to 70% of the disintegrant(s), of the sweetener or sweeteners, of the diluent(s), lubricants, glidants and flavoring(s), and the compression of the resulting mixture.

The invention will be understood more clearly by means of the additional description which follows and which refers to exemplary embodiments of dispersible tablets in accordance with the invention. It goes without saying, however, that these examples are given solely by way of illustration of the invention and do not in any way constitute a limitation thereto.

EXAMPLE 1

Dispersible Tablets Containing Spiramycin Base 3 MIU*; Mint Flavor

Dispersible tablets weighing 2000 mg each and containing 3 MIU of spiramycin base are prepared from the following ingredients:

| | | |
|---|---|---|
| Spiramycin base | 750 mg(3 MIU)** | 37.5% |
| Crospovidone | 45 mg | 2.25% |
| Croscarmellose sodium | 85 mg | 4.25% |
| Polysorbate | 7.5 mg | 0.38% |
| Microcrystalline cellulose | 762.5 mg*** | 38.12% |
| Aspartame | 160 mg | 8.00% |
| Saccharin sodium | 80 mg | 4.00% |
| Mint flavor | 80 mg | 4.00% |
| Colloidal silica | 10 mg | 0.5% |
| Magnesium stearate | 20 mg | 1.00% |

*MIU corresponds to Millions of International Units and gives the activity of an antibiotic; it is measured by comparing the inhibition of the growth of sensitive microorganisms which is induced by known concentrations of the antibiotic to be tested and of a reference substance (Phamacopeia 1997).
**The quantity of spiramycin is adjusted according to its titer.
***The quantity of microcrystalline cellulose is adjusted according to the quantity of spiramycin in order to obtain a final mass of 2000 mg.

EXAMPLE 2

Dispersible Tablets Containing Spiramycin Base 3 MIU*; Vanilla/Caramel Flavor

Dispersible tablets weighing 2000 mg each and containing 3 MIU of spiramycin base are prepared from the following ingredients:

| | | |
|---|---|---|
| Spiramycin base | 750 mg(3 MIU)* | 37.5% |
| Crospovidone | 45 mg | 2.25% |
| Croscarmellose sodium | 85 mg | 4.25% |
| Polysorbate | 7.5 mg | 0.38% |
| Microcrystalline cellulose | 682.5 mg** | 34.12% |
| Aspartame | 160 mg | 8.00% |
| Saccharin sodium | 80 mg | 4.00% |
| Vanilla/caramel flavor | 160 mg | 8.00% |
| Colloidal silica | 10 mg | 0.5% |
| Magnesium stearate | 20 mg | 1.00% |

*The quantity of spiramycin is adjusted according to its titer.
**The quantity of microcrystalline cellulose is adjusted according to the quantity of spiramycin in order to obtain a final mass of 2000 mg.

EXAMPLE 3

Dispersible Tablets Containing Spiramycin Base 0.75 MIU in Combination with Metronidazole; Mint Flavor Dispersible tablets weighing 1000 mg each and containing 0.75 MIU of spiramycin base are prepared from the following ingredients:

| | | |
|---|---|---|
| Spiramycin base | 190 mg(0.75 MIU)* | 19% |
| Metronidazole | 125 mg | 12.5% |
| Polyvinylpyrrolidone | 22.5 mg | 2.25% |
| Croscarmellose sodium | 75 mg | 7.5% |
| Polysorbate | 3.8 mg | 0.38% |
| Microcrystalline cellulose | 448.7 mg** | 44.87% |
| Aspartame | 60 mg | 6% |
| Saccharin sodium | 30 mg | 3.00% |
| Mint flavor | 30 mg | 3.00% |
| Colloidal silica | 5 mg | 0.5% |
| Magnesium stearate | 10 mg | 1.00% |

*The quantity of spiramycin is adjusted according to its titer.
**The quantity of microcrystalline cellulose is adjusted according to the quantity of spiramycin in order to obtain a final mass of 1000 mg.

EXAMPLE 4

Dispersible Tablets Containing Clarithromycin Base; Mint Flavor

Dispersible tablets weighing 1000 mg each and containing 250 mg of clarithromycin base are prepared with the following ingredients:

| | | |
|---|---|---|
| Clarithromycin base | 250 mg | 25% |
| Crospovidone | 22.5 mg | 2.25% |
| Croscarmellose sodium | 62.5 mg | 6.25% |
| Polysorbate | 3.8 mg | 0.38% |
| Microcrystalline cellulose | 566.2 mg | 56.62% |
| Aspartame | 40 mg | 4.00% |
| Saccharin sodium | 20 mg | 2.00% |
| Mint flavor | 20 mg | 2.00% |
| Colloidal silica | 5 mg | 0.5% |
| Magnesium stearate | 10 mg | 1.00% |

EXAMPLE 5

Dispersible Tablets Containing Roxithromycin Base; Mint Flavor

Dispersible tablets weighing 1000 mg each and containing 150 mg of roxithromycin base are prepared from the following ingredients:

| | | |
|---|---|---|
| Roxithromycin base | 150 mg | 15% |
| Crospovidone | 22.5 mg | 2.25% |
| Croscarmellose sodium | 62.5 mg | 6.25% |
| Polysorbate | 3.8 mg | 0.38% |
| Microcrystalline cellulose | 666.2 mg | 66.62% |
| Aspartame | 40 mg | 4.00% |
| Saccharin sodium | 20 mg | 2.00% |
| Mint flavor | 20 mg | 2.00% |
| Colloidal silica | 5 mg | 0.5% |
| Magnesium stearate | 10 mg | 1.00% |

All the tablets prepared in accordance with examples 1 to 5 proved capable of disintegrating completely in less than 3 minutes once placed in a glass of water. Moreover, tests aimed at comparing the taste of the suspensions obtained by dispersing the tablets prepared in accordance with examples 1 to 3 and 5 in relation to that of suspensions obtained by dispersion of the dispersible galenic forms currently available for the same macrolides (Rovamycin®, granules for spiramycin, and Rulid® 50 mg, powder for oral suspension for roxithromycin) showed the tablets according to the invention make it possible to mask the bitterness of the macrolides better and lead to oral suspensions whose taste is notably more pleasant.

Although embodiments, compositions, examples, method (process) steps for preparing the inventive dispersible tablets, and uses of the invention have been shown and described, it is to be understood that various modifications and rearrangements of the composition and method steps of the invention, as well other examples and uses of the invention, can be made by those skilled in the art without departing from the novel spirit and scope of this invention.

What is claimed is:

1. A dispersible tablet containing a macrolide as active ingredient, alone or in combination with another active ingredient, characterized in that the macrolide is not coated, is present in base form and is chosen from the group consisting of pristinamycin, azithromycin and clarithromycin, in proportions of between 20% and 60% of the total weight of the tablet; roxithromycin in proportions of between 15% and 60% of the total weight of the tablet and spiramycin in proportions of between 19% and 60% of the total weight of the tablet; and in that it comprises, as disintegrant, a mixture of polyvinylpyrrolidone and croscarmelose sodium in proportions of between 1% and 25% of the total weight of said tablet, and at least one sweetener.

2. The dispersible tablet as claimed in claim 1, characterized in that the macrolide is chosen from the group consisting of azithromycin, roxithromycin and clarithromycin.

3. The dispersible tablet as claimed in claim 1, characterized in that the ratio of the mixture of polyvinylpyrrolidone to croscarmellose sodium is between 1:1 and 4:1.

4. The dispersible tablet as claimed in claim 1, characterized in that a sweetener is chosen from the group consisting of aspartame, saccharin sodium, acesulfame potassium, ammonium glycerinate and mixtures thereof.

5. The dispersible tablet as claimed in claim 4, characterized in that it contains the mixture of two sweeteners in a ratio of between 1:1 and 2:1, said mixture representing, by weight, between 1 and 20% of the total weight of said tablet.

6. The dispersible tablet as claimed in claim 1, characterized in that the macrolide is combined with a nitroimidazole derivative.

7. The dispersible tablet as claimed in claim 6, characterized in that the macrolide is spiramycin and the nitroimidazole derivative is metronidazole.

8. The dispersible tablet as claimed in claim 1, characterized in that it contains, in addition, at least one excipient chosen from the group consisting of diluents, surfactants, lubricants, glidants, and one or more flavorings.

9. The dispersible tablet as claimed in claim 8, characterized in that it contains at least one diluent chosen from the group consisting of microcrystalline cellulose, lactose, hydroxypropyl methyl cellulose and pregelatinized starch.

10. The dispersible tablet as claimed in claim 9, characterized in that the microcrystalline cellulose is present in proportions of between 5% and 50% of the total weight of said tablet.

11. The dispersible tablet as claimed in claim 8, characterized in that it contains at least one surfactant chosen from the group consisting of polysorbates and sodium lauryl sulfate, in proportions of between 0.1% and 3% of the total weight of said tablet.

12. The dispersible tablet as claimed in claim 8, characterized in that it contains magnesium stearate as lubricant, in proportions of between 0.5% and 3% of the total weight of said tablet, and a glidant in proportions of between 0.1% and 3% of the total weight of said tablet.

13. The dispersible tablet as claimed in claim 12, characterized in that it contains colloidal silica as glidant.

14. The dispersible tablet as claimed in claim 8, characterized in that it contains at least one flavoring chosen from the group consisting of mint, chocolate, caramel, vanilla, strawberry or licorice flavors and mixtures thereof, in proportions of between 0.5% and 15% of the total weight of said tablet.

15. The dispersible tablet as claimed in claim 14, characterized in that the mint flavor is present in proportions of between 1% and 7% of the total weight of said tablet, while the vanilla/caramel flavor is present in proportions of between 1% and 10% of the total weight of said tablet.

16. A method for preparing a dispersible tablet as claimed in claim 1, characterized in that it comprises:

the mixing of the active ingredient(s) with 30% to 60% of the quantity of disintegrant(s) intended to be present in the tablets, the wet granulation of the resulting mixture in preparation of a wetting liquid containing water and at least one surfactant, the drying of the granules thus obtained, the dry addition of the remaining 40 to 70% of the disintegrant(s), of the sweetener or sweeteners, of the diluent(s), lubricants, glidants and flavoring(s), and the compression of the resulting mixture.

* * * * *